United States Patent [19]

Shoesmith, deceased et al.

[11] Patent Number: Plant 6,530

[45] Date of Patent: Jan. 10, 1989

[54] CHRYSANTHEMUM PLANT NAMED CADET

[75] Inventors: Leonard H. Shoesmith, deceased, late of Woking, England, by May Victoria Shoesmith, executrix; Peter S. Hesse, Bradenton, Fla.

[73] Assignee: Ball Pan Am Plant Company, Parrish, Fla.

[21] Appl. No.: 55,597

[22] Filed: May 29, 1987

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Cadet, characterized by its bright yellow ray floret color, almost fully double flower form, jagged or uneven ray floret tips which give the cultivar a carnation-like appearance, cushion growth habit, 8 week flowering response, and by its adaptability to outdoor or commercial pot programs.

1 Drawing Sheet

The present invention comprises a new and distinct cultivar of Chrysanthemum, botanically known as *Chrysanthemum morifolium,* Ramat., and referred to by the cultivar name Cadet.

Cadet is a product of a planned breeding program which had the objective of creating new Chrysanthemum cultivars having bright yellow flower color, cushion growth habit, and the ability to perform well in outdoor garden programs as well as in 4½" to 1 gallon pot mum programs. Such traits in combination were not present or needed improvement in previously available commercial cultivars.

Cadet was originated from a hybridization made in a controlled breeding program in Westfield, Woking, England by Leonard H. Shoesmith in 1980. Both the male and female parents are unknown at this time. Cadet was discovered and selected as one flowering plant within the progeny of the stated parentage by Peter S. Hesse in November 1981 in a controlled environment in Parrish, Fla.

The first act of asexual reproduction of Cadet was accomplished when vegetative cuttings were taken from the initial selection in February 1982 in a controlled environment in Parrish, Fla. by a technician working under formulations established and supervised by Peter S. Hesse. Horticultural examination of selected units initiated in April 1982 has demonstrated that the combination of characteristics as herein disclosed for Cadet are firmly fixed and are retained through successive generations of asexual reproduction.

Cadet has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Cadet, which, in combination, distinguish this Chrysanthemum as a new and distinct cultivar:

1. Bright yellow ray floret color.
2. Almost fully double flower form, with only a few disc florets present.

3. Fully expanded ray florets are 15–24 mm long and 4–5 mm wide.
4. Capitulum is 30–45 mm in diameter.
5. The apex of the ray florets is unevenly toothed, giving the flower a carnation-like appearance.
6. Flowering 8 weeks after the onset of long days.
7. Performs well in the outdoor garden.
8. Excellent production in 4½" to 1 gallon containers.
9. Cushion growth habit.

Of the many commercial cultivars known to the present inventors, the most similar in comparison to Cadet is Minn-Yellow, an unpatented but well known commercial cultivar.

In comparison to Minn-Yellow, Cadet has a one week slower flowering response, brighter yellow flower color, and its flower petals are ragged at the tips as compared with the petal tips of Minn-Yellow, which are smooth. The overall flower form of both cultivars is somewhat shaggy-like in appearance, although this is more noticeable in Cadet due to its ragged petal tips.

The accompanying photographic drawing shows typical inflorescence and leaf characteristics of Cadet. The photograph is in black and white, with several flowers being colored to accurately depict true flower color.

In the following description, color references are made to The Royal Horticultural Society Colour Chart. The color values were determined between 10:00 and 10:30 a.m. on July 7, 1986 under fluorescent lighting at Parrish, Fla.

Classification:

*Botanical.*—*Chrysanthemum morifolium,* Ramat., cv. Cadet.

*Commercial.*—Garden mum or commercial pot mum.

INFLORESCENCE

A. Capitulum:

*Form.*—Flat.

*Type.*—Double.

*Diameter across face.*—3–4.5 cm.

B. Corolla of ray florets:

*Color (general tonality from a distance of three meters).*—Bright yellow.

*Color (upper surface).*—5A.

*Color* (*under surface*).—5B.

C. Corolla of disc florets:

*Color* (*mature*).—Yellow, very few present.

*Color* (*immature*).—Yellow green, very few present.

D. Reproductive organs:

*Androecium.*—Present in disc florets only.

*Gynoecium.*—Present in both ray and disc florets.

PLANT

A. General appearance:

*Height.*—Approximately 20 cm when grown in a 4½" pot. Height can vary upon growing conditions, growth regulator applications and other culture practices.

B. Foliage:

*Color* (*upper surface*).—147A.

*Color* (*under surface*).—147B.

*Shape.*—Ovate with cleft margins.

We claim:

1. A new and distinct Chrysanthemum plant named Cadet, as illustrated and described, and particularly characterized by its bright yellow ray floret color, almost fully double flower form, jagged or uneven ray floret tips which give the cultivar a carnation-like appearance, cushion growth habit, 8 week flowering response, and by its adaptability to outdoor or commercial pot programs.

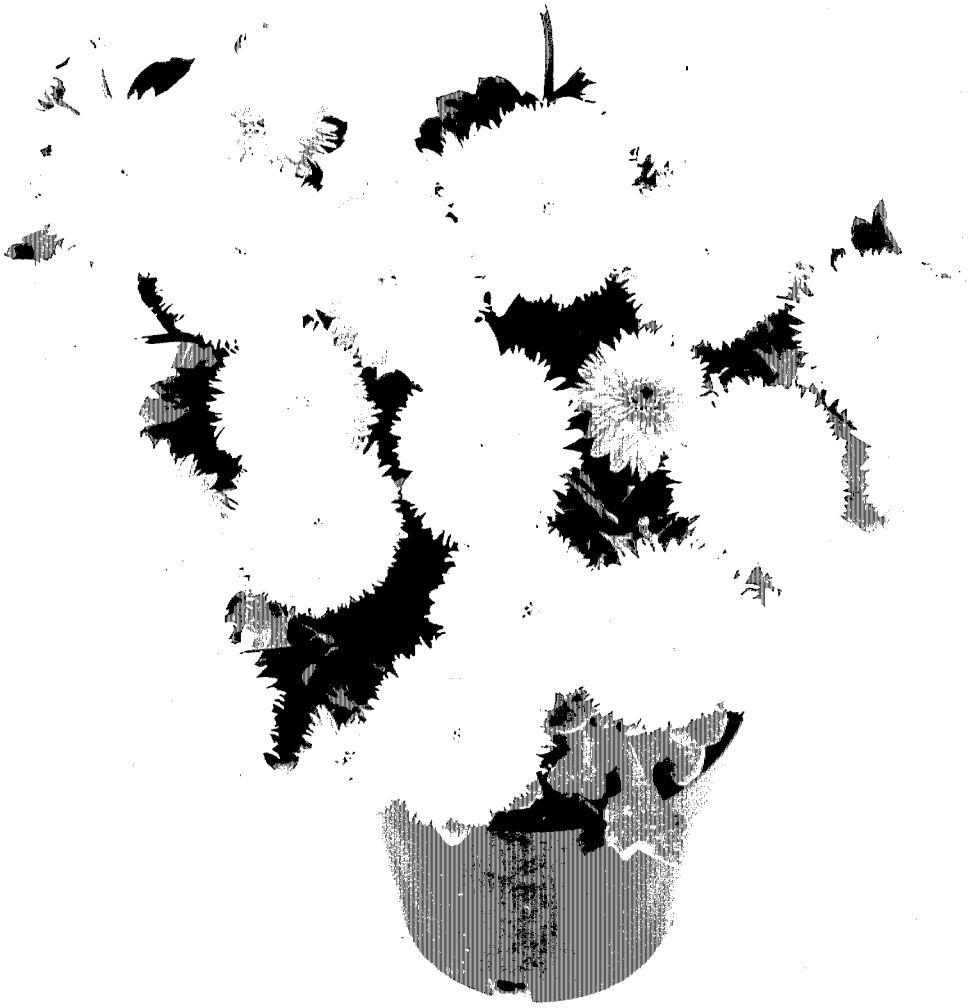

* * * * *